United States Patent [19]

Soldner et al.

[11] 4,119,891
[45] Oct. 10, 1978

[54] OSCILLOSCOPE FOR THE IMAGE DISPLAY OF SECTIONAL PLANES OF A BODY

[75] Inventors: Richard Soldner, Erlangen; Rudolf Rattmann, Herzogenaurach, both of Germany

[73] Assignee: Siemens Aktiengesellschaft, Berlin & Munich, Germany

[21] Appl. No.: 745,228

[22] Filed: Nov. 26, 1976

[30] Foreign Application Priority Data

Dec. 19, 1975 [DE] Fed. Rep. of Germany ....... 2557528

[51] Int. Cl.$^2$ ............................................. H01J 29/70
[52] U.S. Cl. .................................. 315/389; 315/397; 315/402
[58] Field of Search ............... 315/370, 371, 389, 396, 315/397, 402; 73/67.9

[56] References Cited

U.S. PATENT DOCUMENTS

| 3,646,393 | 2/1972 | Tarr ........................................ 315/403 |
| 3,781,589 | 12/1973 | Brockmann ........................... 315/387 |
| 3,786,303 | 1/1974 | Hilburn ................................. 315/397 |
| 3,887,829 | 6/1975 | Owens, Jr. ............................. 315/389 |
| 3,887,842 | 6/1975 | Owens, Jr. et al. .................... 315/397 |
| 3,890,542 | 6/1975 | Zimmermann ........................ 315/389 |
| 3,902,357 | 9/1975 | Soldner et al. ........................ 73/67.9 |
| 3,965,390 | 6/1976 | Spencer, Jr. ........................... 315/389 |
| 4,031,411 | 6/1977 | Schat et al. ........................... 315/370 |

FOREIGN PATENT DOCUMENTS

| 1,353,537 | 5/1974 | United Kingdom. |
| 1,043,376 | 9/1966 | United Kingdom. |
| 1,341,224 | 1/1971 | United Kingdom. |

OTHER PUBLICATIONS

Wilcox, "A Complete Monolithic Vertical-Deflection System for Television", *IEEE Transactions on Broadcast and Television Receivers*, vol. BTR-17, No. 4, pp. 256-262, Nov. 1971.

*Primary Examiner*—Richard A. Farley
*Assistant Examiner*—Lawrence Goodwin
*Attorney, Agent, or Firm*—Hill, Gross, Simpson, Van Santen, Steadman, Chiara & Simpson

[57] ABSTRACT

A line sweep magnetic deflection system is triggered to display ultrasonic echo impulses during line by line scanning of a body region. Each trigger impulse produces a nonlinear saw-tooth voltage waveform as a function of time which when converted to a corresponding current waveform in the deflection coil produces a constant line deflection velocity for accurate display of echo signals in spite of nonlinearities in the electron optics of the oscilloscope, for example. High gain differential amplifier means force the coil current to conform to the voltage waveform during active line trace, and deviations during retrace intervals cause the application of an overvoltage to the coil driver stage, blocking a normal operating supply voltage therefor, and rapidly driving the coil to its initial energy state, thereby enabling a higher line sweep frequency with consequent optimum display resolution.

16 Claims, 1 Drawing Figure

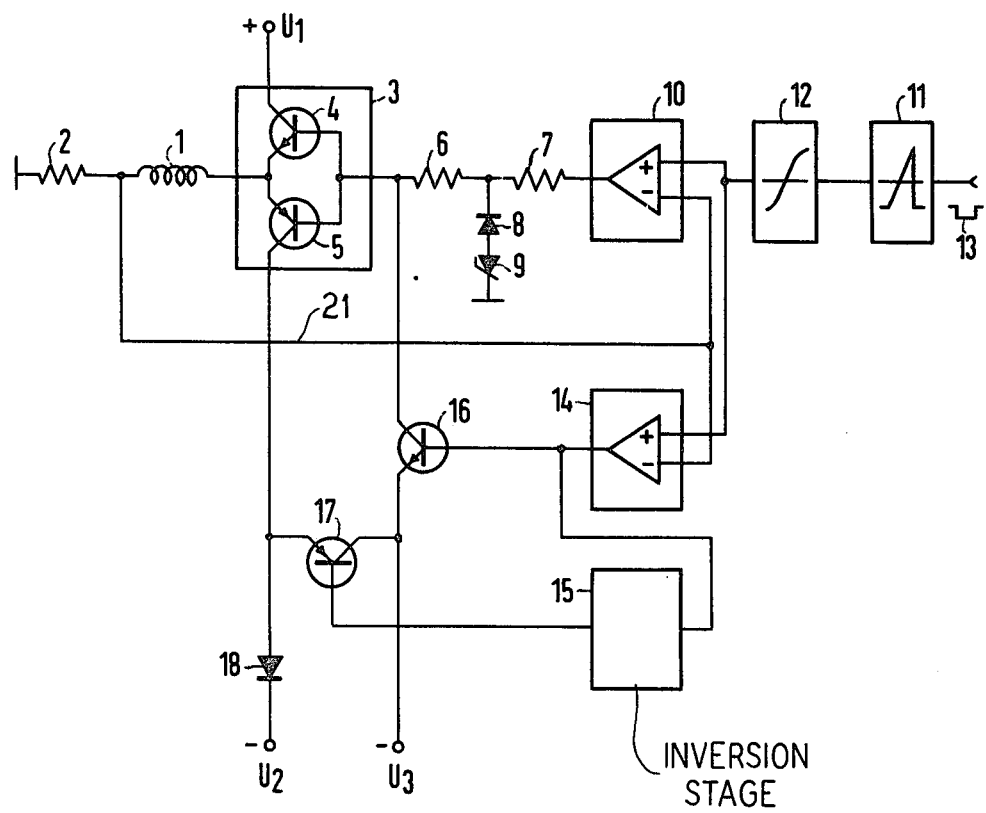

OSCILLOSCOPE FOR THE IMAGE DISPLAY OF SECTIONAL PLANES OF A BODY

BACKGROUND OF THE INVENTION

This invention relates to an oscilloscope for the display of sectional planes of a body by means of forming an image of the echo impulses received pursuant to a linear scanning of the body with ultrasonic impulses, with a line rate deflecting system for producing a magnetic deflection field of an image display tube, the active line trace being triggered by a control impulse produced in dependence upon a transmitted ultrasonic impulse.

A prior art oscilloscope of this type is characterized by a line rate deflecting system comprising a total of two circuits for supplying current to the line deflection coil. The first circuit with a first voltage source delivers a constant biasing current of such polarity that, due to the magnetic field of the line deflection coil, the electron beam of the display tube is retained in the non-triggered state in an inoperative position on the left side of the tube picture screen. In contrast thereto, the second circuit serves the purpose of producing the line synchronizing impulse in the following manner. With the occurrence of a trigger impulse, a transistor is actuated to the conductive state, and the line deflection coil is thereby connected to a second voltage source having a polarity opposite that of the voltage source for the biasing current. The linear rise in current in the deflection coil as effected thereby, in superposition with the biasing current, then represents the ascending flank of the sweep current impulse for horizontal deflection of the electron beam by means of the corresponding magnetic field of the line deflection coil. In contrast thereto, the negative going flank of the current impulse which returns the electron beam to the initial rest position results by blocking of the transistor due to current interruption by means of a diode. However, in oscilloscopes of the above type, there are further essential requirements in addition to the triggerability of the line sweep. One of these requirements is that in order to preserve the linearity of the image display or recording, the respective line deflection must proceed with absolutely uniform speed over the entire height or extent of the picture, independently of varying transit paths of the electron beam to the tube picture screen (the transit paths being longer at the screen edges than in the center of the screen). An additional requirement is that, in the interest of close line intervals (optimum line frequency for the purpose of an optimum image resolution), the return time of the electron beam to the initial position, that is the return sweep period of the deflection generator, should be as brief as possible. Finally, the entire deflection system should exhibit the lowest possible power loss. Practice has shown that a line-sweep coil deflection system such as is used in oscilloscopes of the above type cannot meet the requirements listed above to the degree desired. Due to the linearity of the rise in current of the line synchronizing impulse, only constant beam deflection speeds are yielded, on the one hand, which, however, are converted to non-uniform line deflection speeds on account of the varying transit paths of the electron beam to the tube picture screen. Line deflection proceeds more rapidly on the edges of the picture screen than in the center of the screen, so that the image points of echo impulses of each line, with the same chronological impulse intervals, succeed one another less rapidly toward the edges of the picture screen than in the center of the picture screen. On the other hand, in the known deflection system, the return sweep period is restricted to finite lower boundary values by time constants which are determined by coil inductance and non-negligible ohmic electric circuit resistances, and it is not possible to obtain a return sweep period below that determined by these time constants. Finally, as a consequence of a constantly flowing, relatively high biasing current, an unnecessarily high power loss also results.

SUMMARY OF THE INVENTION

It is an object of the present invention to construct a line deflection system for an oscilloscope of the above type which continues to be triggerable but which, in constrast with the known systems, in addition to an optimum minimal power loss, also guarantees absolutely constant line deflection speeds while, at the same time, having the shortest return sweep periods in returning the electron beam to the initial position.

In an oscilloscope of the type initially cited, the problem is solved in accordance with the invention in that the line-sweep coil deflection system comprises a differential amplifier connected to control the horizontal deflection coil, the differential amplifier receiving as input a nonlinear line scanning voltage which is randomly controllable as to its wave form as a function of time, such wave form being provided by a triggerable horizontal time base generator, the differential amplifier also having an input for receiving a feedback voltage which is strictly proportional to the current in the line sweep coil, the line sweep deflecting system further having an overvoltage circuit for supplying an overvoltage to the line deflecting coil during line retrace intervals in response to predetermined variations in the input voltages to the differential amplifier.

The overvoltage circuit of the line sweep coil deflection system according to the invention forces nonlinear current increases in the coil to proceed rigidly according to the pattern of the nonlinear progression of the saw-tooth voltage supplied by the horizontal time base generator. If the saw-tooth line sweep voltage increase is selected such that the line deflection current resulting therefrom deflects the electron beam of the tube more slowly in the marginal zones of the tube picture screen than in the center of the tube picture screen, the result is a constant horizontal deflection speed of the electron beam over the tube picture screen. Accordingly, the image point representation of echo impulses along each line proceeds true to scale, and the linearity of the image displayed or recorded is thus guaranteed. However, in addition to constant line deflection speed, the shortest return sweep periods of the electron beam to the initial position also simultaneously result due to superimposing of the overvoltage on the end of line sweep wave form. This renders possible a smaller line interval and, with a greater line density, also an improved image resolution. As stated, however, connection of the overvoltage (in the amount of minus 60 volts, for example) proceeds solely during the short return sweep interval of the electron beam during return of the electron beam to its initial position in preparation for a further active line sweep cycle. However, in the course of the actual line deflection, the voltage supply can be kept relatively low, for example in a range between minus twelve volts and plus twelve volts, corresponding to the lower speed of increase of the line sweep impulse. In contrast with the deflection system of the oscilloscope of the known type, wherein a 230 volt direct current source is required in order to produce the biasing current, and an additional 30 volt direct current voltage source is required in order to produce the actual line sweep, the deflection system according to the present invention operates with a lower energy expenditure and thereby also with a correspondingly lower power loss. In a preferred embodiment of the invention, the line sweep generator should consist of a triggerable saw-tooth generator with a tangential distortion corrector connected at its output, whereby, in the simplest form, a VDR-resistance can serve as the tangential distortion corrector. A line rate generator constructed in this manner produces a line scanning voltage whose ascending flank, after an initial relatively slower increase, increases more rapidly toward the center as a function of time, and subsequently levels off again toward the end of the active line sweep interval. However, as already indicated above, it is precisely such a saw-tooth voltage gradient as a function of time which leads to a uniform horizontal deflection speed at the picture screen of the electron beam tube. In addition, a transistor output stage connected between the coil and the first differential amplifier, with an operating voltage which is much lower as compared with the overvoltage, can serve the purpose of controlling the sweep current of the line deflection coil. This transistor output stage can be decoupled from its operating voltage and connected to the overvoltage by means of the overvoltage circuit when there are variations in the input voltages of the differential amplifier. The connecting and disconnecting again of overvoltages with respect to the deflection system of a magnetically deflected picture tube for the purpose of shortening the transport periods of an electron beam from one position to another is indeed already prior art through the British Letters Pat. No. 1,341,224. However, in the transistor output amplifier described therein, the overvoltage which is to be intermittently connected does not serve the purpose of shortening the return sweep period of the electron beam into the initial position specifically upon termination of a line sweep. On the contrary, the overvoltage serves the purpose of effecting a more rapid changeover of the electron beam from one signal channel to the following in the cadence of a signal changeover switch which alternately changes over the vertical deflection system of the picture tube between two varying signals which are to be reproduced or displayed in respective channels positioned one beneath the other. In addition, a switching signal which is obtained by means of a comparison of a coil feedback voltage with the original deflection voltage also does not serve as the switch-on impulse for the overvoltage, as in the present inventive instance. On the contrary, an induction impulse of the deflection coil, produced directly in the coil with the changeover of the electron beam from one channel to the following channel, serves as the connecting impulse. Thus, the overvoltage connecting circuit of the British Letters Pat. No. 1,341,224 and of the present invention serve different practical purposes, and they also differ from one another in terms of a solution.

Other objects, features and advantages of the present invention will be apparent from the following description of an exemplary embodiment, taken in connection with the accompanying drawing.

BRIEF DESCRIPTION OF THE DRAWING

The single FIGURE represents a basic circuit diagram showing an exemplary embodiment in accordance with the present invention.

DETAILED DESCRIPTION

In the single FIGURE, reference numeral 1 designates the line deflection coil of a magnetically deflected oscilloscope. (Illustration of other component parts of the oscilloscope such as the tube, picture screen, vertical deflection system, Wehnelt cylinder, etc., for example, has been dispensed with for reasons of clarity, since these are generally known. An ultrasound examination system operating according to the impulse echo process and used particularly for medical purposes is illustrated in U.S. Pat. No. 3,902,357 issued Sept. 2, 1975, such system including the components of an oscilloscope, and showing an example of a system which can incorporate the circuitry of a magnetic deflection system in accordance with the present invention.) An ohmic resistance 2 is connected on the output side of, and in series with, the line deflecting coil 1.

For the purpose of current actuation of deflection coil means 1, there is provided a transistor output stage 3 having its output connected with the coil means 1. The transistor output stage has two transistors 4 and 5 in emitter follower connection. The operating voltage of the output stage 3 is provided by operating voltage supply means as represented by terminals plus $U_1$ and minus $U_2$. By way of example, the voltage at terminal plus $U_1$ may be plus twelve volts, and the voltage at terminal $U_2$ may be minus twelve volts. A differential amplifier 10 is connected in circuit for controlling the output stage 3 via an amplitude limiter circuit comprising ohmic resistances 6 and 7, a simple semiconductor diode 8 and a Zener diode 9. A saw-tooth generator is connected with the non-inverting input of differential amplifier 10 and comprises a triggerable saw-tooth generator 11 for providing a wave form as indicated, at its output, a tangential distortion corrector 12 being connected with the output of the generator 11 and having a voltage input-output transfer characteristic as indicated. In particular, in response to a triggering impulse 13, generator 11 supplies a voltage waveform which begins from an initial negative voltage maximum, and progressively increases as a function of time with a constant slope corresponding to the desired rate of deflection of the electron beam of the cathode ray oscilloscope, for example. The saw-tooth output wave form from generator 11 reaches a maximum positive value and then abruptly returns to the maximum negative rest voltage level where it remains pending receipt of a further trigger impulse. The transfer function of the tangential distortion corrector is such that at the maximum negative level of the output voltage from generator 11, the slope of the output of circuit 12 as a function of time is nonlinear and provides a progressively increasing positive slope. In the midrange of voltages of the saw-tooth voltage waveform supplied at the input to circuit 12, the output of the circuit 12 has essentially the same slope as the input waveform as a function of time, but as the input voltage of the saw-tooth waveform approaches the maximum positive level, the transfer function exhibits a decreasing slope so that the output voltage from circuit 12 has a progressively decreasing slope as a function of time as the input voltage reaches a positive maximum. When the input voltage waveform abruptly returns to the maximum negative voltage level, the output of circuit 12 correspondingly abruptly returns to a corresponding maximum negative level and supplies such steady maximum negative voltage to the non-inverting input of differential amplifier 10 until generator 11 is triggered by a further impulse 13. By way of example, tangential distortion corrector circuit 12 may comprise voltage dependent resistance means (VDR-resistance), one varistor, for example, controlling the output for negative voltage values of the input, and the other varistor controlling the output for positive voltage values, each resistance means for example comprising a semiconductor diode and bias resistance series circuit, the diodes being oppositely poled, and being biased so that one series circuit begins to conduct near the negative maximum input voltage level and so that the other oppositely poled series circuit begins to conduct as the input voltage level approaches the positive maximum voltage level. Such circuits are well known per se, for example in the field of electronic analog computation.

The inverting input of differential amplifier 10 is connected to the ohmic series resistance 2 associated with the deflection coil 1 via a feedback line 21. In addition, there is a second differential amplifier 14 having respective inputs connected in parallel with the inputs of differential amplifier 10, the second differential amplifier 14 having its output connected directly to the base of a npn-switching transistor 16 and also connected to the base of a pnp-transistor 17 via an inversion stage 15. Switching transistors 16 and 17 respectively serve the purpose of connecting an overvoltage $U_3$ of minus sixty volts, for example, to the base of transistors 4 and 5 of the emitter follower in the output stage 3, on the one hand, and to the collector of transistor 5, on the other hand. A semiconductor diode 18 is poled so as to disconnect the operating voltage (minus $U_2$) of the transistor output stage 3 upon connection of the overvoltage (minus $U_3$).

The mode of operation of the basic circuit is as follows with regard to the production of a line sweep current in the coil 1:

The saw-tooth produced in saw-tooth generator 11 with the occurrence of a trigger impulse 13, is, after tangential distortion correction in tangential distortion corrector 12, delivered via the non-inverting input of differential amplifer 10 and via the transistor output stage 3 to the deflecting coil 1 with the result that a corresponding voltage waveform is applied to the series circuit including coil 1 and feedback resistance 2. In contrast thereto, the feedback voltage obtained from resistance 2, which is proportional to current $I_H$ through deflection coil 1 is fed back to the inverting input of differential amplifier 10. With a correspondingly high loop amplification through the amplifier 10, a current gradient or waveform results in deflecting coil 1 which, within the operating limits of transistor output stage 3, precisely corresponds to the voltage gradient on the output of tangential distortion corrector 12. In the ascending phase of the line sweep voltage, both input voltages on differential amplifier 10 are equally great (differential amplifier 10 is adjusted to the amplification output to input voltage ratio of one to one). The output signal of the parallel-connected second differential amplifier 14 is thus at a low value, and transistors 16 and 17 are blocked. Thus, the input to the inversion stage 15 is at a low value, and the output of the inversion stage 15 serves to block transistor 17. However, at the instant of switching back the input line scan voltage from corrector 12 to the negative initial level (the rear flank of the line sweep impulses), a differential voltage results on the input of differential amplifier 10 and also on the input to differential amplifier 14. The latter produces an output pulse which places the transistors 16 and 17 in the conductive state. Thus, the output pulse from differential amplifier 14 is supplied to the input of inversion stage 15, and the corresponding output of the inversion stage 15 places transistor 17 in the conductive state. By switching off operating voltage $U_2$ by means of diode 18, transistors 4 and 5 of transistor output stage 3 are now supplied with the overvoltage $U_3$ of minus sixty volts at their base input side as well as on their collector output side. This effects an immediate decrease in current in the coil 1, and thus a return of the electron beam to the initial position in the shortest return sweep time period. Once the initial position has been reached, equally great voltages again result on the inverting and non-inverting inputs of the respective differential amplifiers 10 and 14, and transistors 16 and 17 are blocked; that is, the overvoltage $U_3$ is switched off.

While there has been disclosed a presently preferred embodiment of the present invention, it will be apparent that many modifications and variations may be effected without departing from the scope of the novel concepts of the present invention.

We claim as our invention:

1. In an image display system for the image-display of sectional regions of a body, wherein control impulses (13) are produced in dependence upon respective transmitted ultrasonic impulses, an oscilloscope for the formation of an image in accordance with sequences of ultrasonic echo impulses received in response to the successive transmitted ultrasonic impulses during linear scanning of the region, comprising a line sweep deflection system including coil means (1) for producing a magnetic deflection field controlling each line trace operation in generating the image, each active line trace interval of the line trace operation being triggered by one of the control impulses (13), and a transistor output stage (3) connected with the coil means (1) for the purpose of controlling current flow therein, characterized by the combination of:

(a) circuit means (10, 14, 15, 16, 17, 18) connected to said output stage (3) for controlling current flow in said coil means (1); said circuit means comprising differential amplifier means (10, 14); said differential amplifier means (10, 14) having feedback means (2) connected therewith for supplying a feedback voltage thereto which is strictly proportional to coil current ($I_H$) in said coil means (1);

(b) said circuit means including a switching circuit (16, 17) having an overvoltage input for supplying an overvoltage input value ($U_3$) and operable for connecting the overvoltage input value ($U_3$) to the coil means (1) for the purpose of providing a flyback interval of each line trace operation, of reduced duration;

(c) a horizontal time base generator (11, 12) connected with said differential amplifier means (10, 14) for controlling said differential amplifier means to produce a tangential-distortion-corrected line sweep voltage; said horizontal time base generator (11, 12) comprising a triggerable sweep voltage generator (11) having a line sweep cycle which is triggered by a control impulse (13) and which generatess a voltage waveform which is not corrected for tangential distortion during each line sweep cycle; and comprising a voltage dependent resistance (VDR) circuit (12) operated by the voltage waveform from the triggerable sweep voltage generator (11) and providing tangential distortion correction in conjunction with the voltage waveform from the triggerable sweep voltage generator (11); and (d) said circuit means having an operating voltage input for supplying an operating voltage ($U_2$) to said transistor output stage (3) which is substantially less said overvoltage input value ($U_3$) during part of each line trace operation; and (e) said differential amplifier means being responsive to a feedback voltage from the feedback means (2) during the flyback interval of each line trace operation for activating said switching circuit (16, 17) to connect said overvoltage input value ($U_3$) to said coil means (1).

2. A system according to claim 1 with said triggerable sweep voltage generator (11) being operable to generate a sawtooth waveform, and said voltage dependent resistance circuit (12) being connected between said triggerable sweep voltage generator (11) and an input of the differential amplifier means for providing said tangential distortion correction.

3. A system according to claim 1 with said differential amplifier means comprising a differential amplifier (14) having one input connected to the output of said voltage dependent resistance circuit (12) and having a second input connected to said feedback means (2), and responsive to a departure of the feedback voltage from the output of said voltage dependent resistance circuit (12) to activate said switching circuit (16, 17).

4. A system according to claim 3, with said triggerable sweep voltage generator (11) being operable to generate a single linear ramp voltage waveform followed by an abrupt return to an initial voltage level in preparation for a further control impulse (13) produced in dependence upon a further transmitted ultrasonic impulse, and said differential amplifier (14) being responsive to the abrupt return to the initial voltage level at the output of the sweep voltage generator (11) to produce an output pulse for actuating said switching circuit (16, 17) to connect said overvoltage input value ($U_3$) to the coil means (1).

5. A system according to claim 4 with said circuit means including means (18) operable to block supply of said operating voltage ($U_2$) from said operating voltage input during actuation of said switching circuit (16, 17) by said differential amplifier (14).

6. A system in accordance with claim 1 with said differential amplifier means comprising a first differential amplifier having respective inputs connected with the generator output and with the feedback means for controlling current flow in said coil means during active line trace intervals, and said circuit means comprising a second differential amplifier having respective inputs connected in parallel with the respective inputs of said first differential amplifier, and connected with said switching circuit and responsive to a predetermined differential between the line sweep voltage and the feedback voltage to connect said overvoltage input value to said coil means.

7. A system in accordance with claim 1 with said transistor output stage having its output connected with said coil means and having its input connected with said differential amplifier means and said circuit means having operating supply means for supplying said operating voltage to said transistor output stage which is substantially lower than the overvoltage supplied according to said overvoltage input value, said transistor output stage being operable in conjunction with said differential amplifier means and said feedback means to supply current to said coil means as a function of time in accordance with the variation of said line sweep voltage as a function of time to produce an essentially linear line scanning displacement for the accurate display of said echo impulses over the entire active line trace intervals.

8. A system in accordance with claim 7 with said circuit means together with said switching circuit being operable to supply said overvoltage to said transistor output stage in place of said operating voltage during flyback intervals.

9. A system in accordance with claim 7 with said transistor output stage comprising two transistors in emitter follower connection and having a base input connected with the output of said differential amplifier means, and said switching circuit comprising overvoltage supply means for supplying said overvoltage to said base input and to a collector of at least one of said transistors.

10. A system in accordance with claim 9 with said switching circuit comprising a first switching transistor between said overvoltage supply means and said base input of said transistor output stage, a second switching transistor between said overvoltage supply means and said collector of said one transistor of said transistor output stage, and said circuit means having means for switching on both of said switching transistors during flyback intervals.

11. A system in accordance with claim 10 with said circuit means further comprising diode means interposed between an output of the second switching transistor and the operating supply means, and poled for decoupling said operating supply means from said collector of said one transistor of said transistor output stage during supply of said overvoltage to said transistor output stage via said second switching transistor.

12. A system in accordance with claim 10 with said first switching transistor being connected with said base input of said two transistors of said transistor output stage and being an npn-transistor, and said differential amplifier means comprising a first differential amplifier having respective inputs connected with the generator output and with the feedback means for controlling current flow in said coil means during active line trace intervals, and said circuit means comprising a second differential amplifier having respective inputs connected in parallel with the respective inputs of said first differential amplifier and having its output directly connected with the input of said first switching transistor for switching on said first switching transistor during flyback intervals in response to a predetermined differential between the line sweep voltage and the feedback voltage.

13. A system in accordance with claim 12 with said circuit means comprising an inversion stage, and said second differential amplifier having its output connected with the input of said second switching transistor via an inversion stage for switching on said second switching transistor in response to a predetermined differential between the line sweep voltage and the feedback voltage.

14. A system in accordance with claim 7 with said circuit means including a diode in series with said operating supply means, and said circuit means being operable to drive said diode into the blocked state so as to decouple the operating supply means from said transistor output stage during connection of the overvoltage to such stage.

15. A system in accordance with claim 7 with said differential amplifier means having an amplitude limiter at its output comprising a Zener diode for blocking of the overvoltage supplied by said switching circuit from said differential amplifier means.

16. A system in accordance with claim 1 with said feedback means comprising an ohmic feedback resistance which is connected in series with said coil means for supplying a feedback voltage which is proportional to the coil current.

* * * * *